United States Patent [19]

Purcell et al.

[11] Patent Number: 4,581,231

[45] Date of Patent: * Apr. 8, 1986

[54] INACTIVATION OF VIRUSES CONTAINING ESSENTIAL LIPIDS

[75] Inventors: Robert H. Purcell, Boyds, Md. D.C.; Stephen M. Feinstone, Washington, D.C.

[73] Assignee: The United States of America as represented by the Secretary of Health and Human Services, Washington, D.C.

[*] Notice: The portion of the term of this patent subsequent to Apr. 16, 2002 has been disclaimed.

[21] Appl. No.: 528,258

[22] Filed: Aug. 31, 1983

Related U.S. Application Data

[63] Continuation-in-part of Ser. No. 386,991, Jun. 10, 1982, Pat. No. 4,511,556.

[51] Int. Cl.⁴ .................. A61K 35/14; C07G 7/00; C12N 7/06
[52] U.S. Cl. .................. 424/101; 260/112 B; 435/238; 514/2
[58] Field of Search .................. 435/235–239; 260/112 B; 424/101, 89, 177, 339, 340, 350; 514/2, 715, 743

[56] References Cited

U.S. PATENT DOCUMENTS

| | | | |
|---|---|---|---|
| 2,798,836 | 7/1957 | Bird et al. | 435/235 |
| 3,847,737 | 11/1974 | Kanarek | 435/238 |
| 4,031,204 | 10/1977 | Davis | 424/90 |
| 4,113,712 | 9/1978 | Funakoshi | 260/112 R |
| 4,139,630 | 2/1979 | Asculai | 424/283 |
| 4,291,020 | 9/1981 | Tabor et al. | 424/89 |
| 4,302,444 | 11/1981 | Baxendale | 424/89 |
| 4,314,997 | 2/1982 | Shanbrom | 424/101 |
| 4,315,919 | 2/1982 | Shanbrom | 424/177 |
| 4,431,633 | 2/1984 | Machlowitz et al. | 424/89 |
| 4,446,134 | 5/1984 | Naito et al. | 424/101 |
| 4,481,189 | 11/1984 | Prince | 424/101 |
| 4,511,556 | 4/1985 | Purcell et al. | 424/101 |

OTHER PUBLICATIONS

Purcell, "The Hepatitis Viruses; An Overview and Historical Perspective", *Viral Hepatitis*, 1981 Franklin Institute Press.
Maramorosch et al., *Methods in Virology*, vol. 2, 1967.

*Primary Examiner*—Robert J. Warden
*Assistant Examiner*—Shawn P. Foley
*Attorney, Agent, or Firm*—John S. Roberts, Jr.

[57] ABSTRACT

A method of inactivating a lipid virus in a protein carrier by contacting said virus for an abbreviated period of time and ambient temperature with a halohydrocarbon solvent or treating agent, preferably chloroform, in an amount of 5% v/v to 50% v/v. Preferred lipid viruses are Hepatitis B virus (HBV) and non-A, non-B Hepatitis (NANBH).

4 Claims, No Drawings

INACTIVATION OF VIRUSES CONTAINING ESSENTIAL LIPIDS

This is a continuation-in-part application of Ser. No. 386,991, filed June 10, 1982, now U.S. Pat. No. 4,511,556.

This application describes a method of inactivating a lipid virus in a protein carrier by contacting said virus for an abbreviated period of time and ambient temperature with a halohydrocarbon solvent or treating agent, preferably chloroform, in an amount of 5% v/v to 50% v/v. Preferred lipid viruses are Hepatitis B virus (HBV) and non-A, non-B Hepatitits (NANBH).

GENERAL BACKGROUND

A selected lipid type virus, viral hepatitis, has been recognized as an important and serious sequela of parenteral exposure to blood and blood components since the early 1940s. It was originally believed that all such blood-associated hepatitis was caused by the serum hepatitis virus (now called the hepatitis B virus, or HBV). Subsequently, the development of sensitive assays for infection with this virus revealed that only approximately ⅓ of transfusion-associated hepatitis was caused by the HBV. It was thought that the remaining hepatitis was caused by the hepatitis A virus. However, the development of sensitive assays for HAV led to the recognition of a new hepatitis virus, the non-A, non-B hepatitis virus (NANB) in 1975. The successful application of sensitive screening tests for HBV to blood donors has resulted in a decrease (but not disappearance) of HBV in transfusion-associated hepatitis; at present approximately 90 percent of such hepatitis is caused by non-A, non-B agents.

Similarly, hepatitis following administration of blood products such a antihemophilic factor was thought to be caused solely by HBV. However, in the late 1970s, the association of NANB agents with administration of antihemophilic factor to hemophiliacs was reported and confirmed. As the transfusion-associated hepatitis, the application of serologic screening methods to plasma donors has resulted in a relative decrease in the importance of HBV in such blood product-associated hepatitis.

Non-A, Non-B hepatitis is the major cause of transfusion associated hepatitis in the United States. Presently less than 10% of post-transfusion cases are caused by the hepatitis B virus. Of the remainder, cytomegalovirus may account for a small proportion but the vast majority are caused by an as yet unidentified agent. There is a large amount of evidence supporting a transmissable agent as the cause of NANBH. This includes transmission studies done in both humans and non-human primates. Chimpanzees and marmoset monkeys have both been shown to be susceptible to infection by at least some NANBH agents. Though very costly and cumbersome to work with, these animals can be used to aid in the characterization of the infectious agent of NANBH.

Unfortunately, serologic tests for the detection of NANB agents are not available for detection of potentially infectious donors because the agents have not been adequately identified and characterized despite extensive efforts to do so. Therefore, blood and blood products remain potential sources for transmission of hepatitis agents to recipients. The resultant hepatitis can be quite serious, even life-threatening, and can result in not only acute hepatitis but also chronic hepatitis in a significant proportion of cases.

For these reasons attempts to inactivate hepatitis agents in blood and blood products have been pursued with vigor. Such approaches have included the use of heat, the addition of anti-HBV antibody, the use of solid immunoadsorbents or other chemical-specific adsorbents, exposure to ultraviolet radiation, the addition of certain inactivating substances, such as beta-propriolactone, surface-active substances, etc. None of the approaches has been entirely successful and some have introduced an added potential risk (e.g., beta-propiolactone is carcinogenic). Failure of these approaches stems from relative resistance of the agents to physical or chemical inactivation, particularly when in the presence of high protein concentrations as occurs with blood products and from limited knowledge about the nature of the hepatitis agents, especially the NANB agents.

As part of a systematic characterization of NANB agents by standardized virologic methods, the present inventors first established that HBV and at least one NANB agent contain lipids essential for the integrity and viability of the viruses. This was established by exposing the viruses to a potent lipid solvent (chloroform) and demonstrating that such chloroform-extracted viruses were rendered non-infectious in a suitable susceptible host, the chimpanzee (*Pan troglodytes*).

It is understood that the present invention applies to all lipid containing NANBH particles which of necessity may be more than one particle as, for example, the more recently discovered delta particle. In exploring other viruses, the inventors also found that any virus which contains an essential lipid can be inactivated by lipid solvents. Thus, this invention expands the parent invention in two significant ways: (1) the class of viruses affected was expanded; and (2) the class of effective lipid solvents applicable in this procedure was expanded.

The present invention relates to a method of inactivating a lipid virus in a protein carrier where said lipid virus is defined to include members of the herpesvirus group (cytomegalovirus, Epstein-Barr virus, herpes zoster virus, herpesvirus type 1 and herpesvirus type 2), the delta agent (a type of non-A, non-B hepatitis virus), and members of other blood-borne virus groups including the togaviruses (including rubella virus) and the bunyaviruses, retroviruses (including the human T-cell leukemia virus), orthomyxoviruses (influenza), paramyxoviruses (measles, mumps), rhabdoviruses (rabies, Marburg agent), and arenaviruses (Lassa fever, other hemorrhagic fevers) as well as other members of the poxvirus group such as vaccinia virus. Other viruses, known or suspected putative agent of acquired immune deficiency syndrome, AIDS, are included as viruses containing essential lipids.

Inactivation is achieved by contacting the virus (in a carrier) for an abbreviated time period at generally ambient temperatures, with a preferred halohydrocarbon treating agent.

This treating agent or solvent is defined to include at least the following: chloroform and chloroform/alkanol mixtures, preferred; dialkyl ethers such as ethyl ether; lower alcohols such as ethanol, methanol, and butanol; and the fluorocarbons (trichlorotrifluoroethane) which include the most common Freon ® or Genetron ® agents such as $CCl_3F$, $CH_2F_2$, $CCl_2F_2$, $CCl_2FCClF_2$. Freons are defined as chlorofluoro carbon of one or two carbon atoms. These may be fluorinated derivatives of methane and ethane. Additional agents are alkylene halides such as dichloroethylene. These treating agents are administered in an amount of approximately 5–50% v/v. The treating agent or solvent may also consist of mixtures of any of the above, with chloroform/lower alkanol being preferred. Although chloroform was used as the inactivating agent to demonstrate the principle of inactivation of hepatitis viruses with a lipid solvent, in practice, these other lipid solvents substitute for chloroform and are effective in inactivating virtually all lipid-containing viruses with the exception of the poxviruses. Thus, the concept of inactivating lipid-containing viruses by extracting their essential lipids with a lipid solvent does not require the preferred chloroform or chloroform/alkanol mixtures (such as chloroform/methanol in a 1:4 to 4:1 ratio), but can be performed with selected other lipid solvents selected on the basis of other characteristics (e.g., lack of toxicity, ease of handling, cost, etc.).

The period of time for treatment is about 10 minutes to five hours and the generally ambient temperature is from about 4° C. to 40° C. The five-hour upper limit may be expandable to any reasonable amount of time since it is the lower range period that determines the efficacy of the process. The treating agent of choice is chloroform, $CHCl_3$, or $CHCl_3$+a lower alkanol (i.e., methanol) and can be used in a method utilizing both extraction of the aqueous blood products by physical means (e.g., centrifugation), or by extraction of the lyophilized dried blood products and the removal of the solvent by other appropriate means such as vacuum evaporation. Generally, these two processes can be distinguished in that in the latter there is a reduction to powder form before treatment, a process which requires greater protection of the products that have been lyophilized.

The process of this invention may require extraction of the virus in dry powder form. However, the virus in its liquid state is preferred. (See Example 2).

The inactivation of HBV and NANBV has been shown in animals such as chimpanzees.

Diethyl ether is an effective inactivating agent for destroying endotoxin or infectivity of non-hepatitis viruses and preventing clotting activation. However, it is a less efficient solvent of lipids. Also, the use of diethyl ether is not recommended for the broader use of the present agents in the nuclization of pox virus; such pox virus may be illustrated by smallpox and vaccinia virus. Not only is diethyl ether noted but other ethers, such as phenoxy, polyethoxy ethanol, and compounds of the general formula $RC_6H_4(OC_2H_4)_nOH$ are also noted.

The present use of chloroform and the Freon or Genetron fluorocarbon agents has been found useful in so-called lipid virus which include HBV and NANBH and also include those virus particles which have a lipid outer coat which is suceptible to removal by treatment.

STATEMENT OF PRIOR ART

A review of the prior art of patents is as follows:
U.S. Pat. No. 4,113,712 to Funakoshi—Utilization of a surfactant such as the Tritons or Tweens for hepatitis B surface antigen particles.
U.S. Pat. No. 4,139,630 Asculai et al—Utilization of non-ionic surfactants as inactivating agents for herpes simplex virus.
U.S. Pat. No. 4,314,997 Shanbrom—A non-denaturing amphiphile used to inactivate hepatitis viruses B and non-A, non-B in amount of 0.25–10% by weight and citing nonanionic, anionic, and cationic surfactants.
U.S. Pat. No. 4,315,919 Shanbrom—Similar disclosure to U.S. Pat. No. 4,314,997 above.
Purcell, "The Hepatitis Viruses: An Overview and Historical Perspective," *Viral Hepatitis*, 1981 International Symposium, ed. Szmuness, Alter and Maynard, Franklin Institute Press, Philadelphia, pp. 3–12.
Philipson, "Water-Organic Solvent Phase Systems," *Methods in Virology*, ed. Maramorosch et al, Volume II, 1967, pp. 235–244.

EXAMPLE 1

Infectious Inoculum. Human plasma, designated H, was drawn by plasmapheresis from a patient with acute post-transfusion NANBH. A portion of the plasma unit had previously been aliquoted into 1 ml vials and a ten-fold dilution series in fetal calf serum from $10^0$ to $10^{-10}$ was prepared, aliquoted into 1 ml quantities in vials and stored at $-70°$ C. until use. This plasma had been shown to have a chimpanzee infectivity titer of at least $10^6$. One ml of this plasma at a $10^{-1}$ dilution was thawed and treated as described below.

A human hepatitis B serum designated MS-2 containing $10^8$ chimpanzee infectious doses per ml had also previously been aliquoted, diluted and stored in a similar way to the NANBH plasma. A one-ml vial of a $10^{-3}$ dilution of the MS-2 serum was thawed and treated as described below.

Control Viruses. Representative chloroform sensitive and resistant viruses were selected as internal and external controls. The internal controls were added directly to the NANBH plasma or to the HBV serum. The internal control viruses were selected because the human serum or plasma containing the hepatitis agents lacked antibody to the control viruses, they would not replicate significantly in chimpanzees which were to be used to assay the hepatitis viruses, and they could be separately assayed each in the presence of the other without interference. Avian influenza virus H.N. was used as the chloroform sensitive internal control. Approximately $10^8$ $TCID_{50}$ was added to each of the hepatitis specimens. The coliphage $\phi \times 174$ was used as the chloroform resistant virus and approximately $10^9$ infectious particles were added to each of the hepatitis specimens. External control viruses were chosen because they represented typical human infectious agents and could be easily assayed. One ml of poliovirus type I LSC vaccine stain containing approximately $10^7$ $TCID_{50}$/ml added to one ml of a 1:10 dilution of fetal calf serum which was then diluted to a final volume of 10 ml served as the chloroform resistant external control virus. One ml of Vaccinia virus Elstree strain containing approximately $10^6$ $TCID_{50}$ was added in a similar way to fetal calf serum and served as the chloroform sensitive external control virus.

Chloroform extraction. Each hepatitis and each external control fetal calf serum preparation was diluted to a final volume of 10 ml or a 1:100 final concentration of serum or plasma. Each 10 ml specimen was then equally aliquoted into two glass screw-cap tubes. To one of the tubes of each specimen, 0.55 ml of chloroform from a freshly opened bottle was added to make a final 10% (v/v) chloroform concentration. All tubes (both those containing and not containing chloroform) were then agitated on a vortex mixer for 10 minutes at room temperature and centrifuged at 1000 RPM for 10 minutes in a Sorvall 3B centrifuge.

The aqueous phase was then carefully pipetted off the interface of the chloroform containing samples and off any pelleted solid material from the samples not containing chloroform. These were aliquoted into 1 ml amounts and stored at −70° C. until assayed.

Viral infectivity assays. Avian influenza virus was assayed on MDCK cells by CPE and hemadsorption with guinea pig red blood cells. Quadruplicate wells of six well plates were inoculated for each dilution of a serial 10-fold dilution series of both the chloroform-treated and sham-treated specimen.

$\phi \times 174$ was assayed by tube dilution (quadruplicate samples) in L broth of each sample to be tested using $E.$ $coli$ 4704 as the host cell.

Vaccinia virus infectivity was assayed by CPE in Vero cells. Quadruplicate wells of 6 well plates were inoculated with serial 10-fold dilutions of the fetal calf serum suspensions containing Vaccinia virus and the relative titers of the chloroform-treated and the sham-treated specimens were compared.

Poliovirus was assayed by CPE in Vero cells in the same manner as the Vaccinia virus.

Chimpanzee inoculations. Two chimpanzees were inoculated with one ml each of the chloroform-treated H plasma. One chimpanzee was inoculated with one ml of the chloroform-treated MS-2 serum. The chimpanzees were monitored for hepatitis by determination of alanine amino transferase (ALT) levels and aspartate amino transferase (AST) levels on weekly plasmapheresis samples. Hepatitis B surface antigen (HBsAg), antibody to HBsAg (anti-HBs) and antibody to hepatitis B core antigen (anti-HBc) were also measured in the plasma from the MS-2 inoculated chimpanzee using commercial radioimmunoassays (Ausria, Ausab and Corab, Abbott Laboratories). In addition, percutaneous liver biopsies were obtained weekly from all chimpanzees. These biopsies were divided into three pieces and fixed in 10% buffered formalin for routine histology, glutaraldehyde for electron microscopy and snap frozen for immunofluorescence.

Diagnosis of hepatitis. Hepatitis was diagnosed in a chimpanzee if the ALT level rose to more than twice the upper limit of normal considered to be forty IU/L. Hepatitis was confirmed by light and electron microscopy on the liver biopsies.

Results:

All the internal and external control viruses reacted to the chloroform treatment as predicted and these results are summarized in Table 1. The avian influenza virus and Vaccinia virus were totally inactivated by chloroform while poliovirus and $\phi \times 174$ were essentially unaffected.

TABLE 1

| Chloroform Extraction of Control Viruses | | |
|---|---|---|
| | Virus Titer $Log_{10}$ $ID_{50}/0.1$ ml | |
| | CHCl Extraction | Sham Extraction** |
| Internal Controls | | |
| $\phi \times 174$ in H Plasma* | 9.0 | 9.5 |
| MS-2 Serum*/Fetal Calf Serum* | 9.0 | 9.5 |
| Avian Influenza Virus in H Plasma* | ≦0.5 | 5.25 |
| MS-2 Serum/Fetal Calf Serum* | ≦0.5 | 5.5 |

TABLE 1-continued

| Chloroform Extraction of Control Viruses | | |
|---|---|---|
| | Virus Titer $Log_{10}$ $ID_{50}/0.1$ ml | |
| | CHCl Extraction | Sham Extraction** |
| External Controls | | |
| Polio Virus Type 1 in Fetal Calf Serum* | 6.5 | 6.5 |
| Vaccinia Virus in Fetal Calf Serum* | ≦0.5 | 5.5 |

*Final total serum or plasma concentration was 1:100 for each virus suspension.
**Without $CHCl_3$ The FIGURE shows the weekly ALT levels in the two chimpanzees (nos. 889 and 947) inoculated with the chloroform-treated H plasma and the one chimpanzee (no. 967) inoculated with the chloroform-treated MS-2 serum. As can be seen, none of these animals developed biochemical evidence of hepatitis. Chimpanzee 967 that was inoculated with the MS-2 plasma did develop anti-HBs but not anti-HBc which is a typical hepatitis B vaccine response indicating HBsAg was in the inoculum but not infectious virus. This animal was probably resistant to infection with live HBV due to its acquisition of anti-HBs. Therefore, it was not challenged with the sham-treated MS-2 plasma. Six months after the initial inoculation, all three of these animals were inoculated with the sham-treated H plasma. As can be seen in the FIGURE, chimpanzee 967 that had no prior exposure to NANBH developed NANBH with a 5-week incubation period. Chimpanzee 889 that had initially been inoculated with the chloroform-treated H plasma also developed NANBH with an incubation period of about 5 weeks after rechallenge with the sham-treated H plasma. However, chimpanzee 947 showed no evidence of hepatitis following either inoculations with the chloroform-treated or sham-treated H plasma.

In a preliminary, uncontrolled experiment, a $10^{-2}$ dilution of the H plasma was still infectious in a chimpanzee after treatment with 5% v/v chloroform. However, this animal had an incubation period of 9.5 weeks, indicating that the virus titer was reduced by the chloroform treatment.

Two human plasma samples in chimpanzees have been studied and one was found to have an infectivity titer of less than $10^2$. The other, however, infected a chimpanzee at a $10^{-6}$ dilution. This relatively high-titered plasma makes certain characterization experiments possible that cannot be done properly with a low-titered inoculum. In this experiment the starting plasma was diluted to a final $10^{-2}$ dilution in order to remove most of the effect of the high concentrations of plasma on the chloroform extraction and still allowed a test to see if $10^4$ chimpanzee infectious units could be inactivated by chloroform. All other chimpanzee inocula that have been reported have a relatively low titer, usually $10^3$ or below. These inocula have much less utility for many characterization experiments.

Hepatitis B virus does not contain a lipid envelope derived from a cell membrane but the coat is composed of lipoprotein. $10^4$ infectious doses of HBV were completely inactivated by treatment with chloroform. Since $10^4$ chimpanzee infectious doses of the H strain of NANB were also inactivated by chloroform, then it was concluded that this agent also contained essential lipid.

EXAMPLE 2

Chloroform Inactivation of Test Viruses in Antihemophilic Fraction

This experiment was performed to determine if chloroform extraction of lyophilized antihemophilic fraction efficiently inactivated 2 lipid-containing viruses, an influenza virus and a pox virus.

Inactivation of these viruses by chloroform extraction of aqueous samples is a standardized procedure. Such chloroform extraction has been employed to inactivate hepatitis B virus and non-A, non-B hepatitis virus in diluted plasma samples. However, a practical application of this procedure to inactivation of hepatitis viruses in commercial antihemophilic fraction could require extraction of the dry powder. The purpose of this protocol was to confirm that such inactivation takes place with "standard" viruses. Avian influenza virus was used because humans lack antibody to this virus. Although the general population has antibody to vaccinia virus, this virus was used with appropriate controls to determine whether traces of antibody in the antihemophilic fraction neutralized the virus.

Commercial AHF was inoculated with a measured amount of avian influenza virus (A/S8) or vaccinia virus (ATCC VR 862 Lot 1) or tissue culture medium (MEM complete with 10% FBS). The product was lyophilized and extracted with chloroform at 1 of 3 temperatures: 5°, 20° or 40° C. The chloroform-extracted and control samples were reconstituted with water for injection and the infectivity titers of influenza virus and vaccinia virus determined in appropriate tissue culture systems.

The tissue culture infectious dose$_{50}$ titer of the avian influenza pool was $10^{7.5}$/ml; the vaccinia virus pool was approximately $10^{6.5}$/ml. Three 30 ml vials of AHF from the same lot were reconstituted with 30 ml of water for injection. To vial #1 was added 1 ml of avian influenza virus inoculum. To vial #2 was added 1 ml of vaccinia virus inoculum. To vial #3 was added 1 ml of tissue culture medium. Each vial was thoroughly mixed (without foaming). 5 ml of each vial was distributed into 6 companion vials, labeled respectively 1A, 1B, 1C, 1D, 1E, 1F, 2A, 2B, 2C, 2D, 2E, 2F, etc. (see Table 1). All 18 vials were lyophilized and sealed. Vials A, B, and C were extracted with chloroform as per the table; vials D, E and F were held at 5°, 20° and 40°, respectively, in the lyophilized state as controls. After chloroform extraction vials 1A through F and vials 2A through F were returned to the Hepatitis Viruses Section for performance of infectivity titrations. The vials were maintained at 5° C. or lower temperature during transit and storage.

Calculation: Av. flu pool (TCID$_{50}$ of $10^{7.5}$) diluted $10^{-1.5} = 10^6$ TCID$_{50}$/ml. Vaccinia pool (TCID$_{50}$ of $10^{6.5}$) diluted $10^{-1.5} = 10^5$ TCID$_{50}$/ml.

Table 2 lists the results of inactivation studies of two lipid-containing viruses in the plasma product, Factor 8, when lipid extraction was carried out at different temperatures. Under the conditions of the experiment (extraction of the dry product for 20 minutes), vaccinia virus was not inactivated at 4° but was partially inactivated at 20° and 40° C. Inactivation of avian influenza virus under similar conditions of treatment was more extensively inactivated (90–99.8%) but inactivation was not complete. Thus, inactivation of lipid-containing viruses in the dry state was more difficult to accomplish than in the liquid state.

The effect of time on inactivation of a lipid-containing virus in the dry state is shown in Table 3. Vaccinia virus was extracted with chloroform in the dry state at room temperature (20° C.) for intervals of time ranging from 20 minutes to 12 hours. Vaccinia virus was 90% inactivated after 20 minutes, 98% inactivated after 2 hours, and completely inactivated after 4 hours or more of exposure to chloroform.

Thus, vaccinia virus, the most difficult of lipid-containing viruses to inactivate, was completely inactivated by exposure to chloroform regardless whether the vaccinia was in the liquid or dry state, but the time required for complete inactivation was greater when the virus was in the dry state. The hepatitis viruses can be expected to be more sensitive to the effect of chloroform and other lipid solvents than vaccinia viruses.

TABLE 2

Effect of Temperature on Chloroform Inactivation of Vaccinia and Influenza Viruses in Factor VIII.

| | | Titer (TCID$_{50}$/ml) | | |
|---|---|---|---|---|
| Virus | Temperature* | Control | CHCl$_3$ | Percent Inactivation |
| Vaccinia | 4° C. | $10^{3.3}$ | $10^{3.5}$ | 0 |
| Vaccinia | 20° C. | $10^{3.3}$ | $10^{2.8}$ | 70 |
| Vaccinia | 40° C. | $10^{3.5}$ | $10^{3.0}$ | 70 |
| Influenza | 4° C. | $10^{3.3}$ | $10^{0.5}$ | 99.8 |
| Influenza | 20° C. | $10^{2.0}$ | $10^{1.0}$ | 90 |
| Influenza | 40° C. | NIΔ | NI | NI |

*Extracted in dry state for 20 min.
ΔResults not interpretable

TABLE 3

Effect of Time on Chloroform Inactivation of Vaccinia Virus in Factor VIII.

| | | Titer (TCID$_{50}$/ml) | |
|---|---|---|---|
| Sample | Duration of Treatment* | Control | CHCl$_3$ |
| 1 | 20 min. | $10^{4.7}$ | $10^{3.7}$ |
| 2 | 2 hr. | $10^{4.3}$ | $10^{2.5}$ |
| 3 | 4 hr. | $10^{4.3}$ | $<10^{0.8}$ |
| 4 | 6 hr. | $10^{4.3}$ | $<10^{0.8}$ |
| 5 | 12 hr. | $10^{4.3}$ | $<10^{0.8}$ |

*Extracted in dry state at room temp.

EXAMPLE 3

Chloroform extraction of lyophilized Factorate

Lyophilized Factor VIII (Factorate—Armour) was extracted with chloroform using three different procedures.

A. 1 gram of Factorate (dry powder) was mixed at 4° C. for 20 minutes with 20 ml of cold chloroform. The chloroform was then removed by filtration and the dry powder was washed on the filter with an additional 10 ml of cold chloroform.

B. 1 gram of Factorate (dry powder) was mixed with 10 ml of cold chloroform at 4° C. for 10 minutes. The chloroform was removed by filtration and the powder was washed on the filter with 5 ml of cold chloroform. This process was then repeated a second time.

C. 1 gram of Factorate (dry powder) was mixed with 20 ml of chloroform at room temperature for 20 minutes. The chloroform was removed by filtration and the dry powder was washed on the filter with 10 ml of chloroform at room temperature.

The samples were reconstituted with deionized water and assayed for Factor VIII:c, Fibronectin, and Fibrinogen (Table 4).

TABLE 4

Factor VIII, Fibronectin and Fibrinogen Activity of Lyophilized Factorate After Chloroform Extraction.

| Sample | Units/ ml | Fibronectin mg/ml | Fibrinogen mg/ml |
|---|---|---|---|
| Control | 9.1 | 1.11 mg | 8.9 mg |
| Room Temp. Extraction | 9.5 | 1.14 mg | 9.3 mg |
| 4° C. 1 × Extracted | 8.9 | 1.19 mg | 9.3 mg |
| 4° C. 2 × Extracted | 9.3 | 1.29 mg | 8.6 mg |

EXAMPLE 4

Inactivation of virus by chloroform or ether

Inoculum dilutions. Hepatitis B virus (1.5 ml) was diluted up to 15 ml with Hanks BSS ($10^{-1}$). This diluted inoculum was kept on wet ice prior to and after treatment.

Chloroform inactivation. 0.6 ml chloroform was added to 5.4 ml of the inoculum and shaken at room temperature for 10 minutes. The upper aqueous phase was carefully pipetted off and 2 ml of dilutions of the aqueous phase ($10^{-0}$, $10^{-1}$, $10^{-2}$, $10^{-3}$) inoculated in rhesus monkeys.

Similar experiments were performed using inocula of vaccinia virus, adenovirus, and herpes virus in concentrations of $10^{-1}$ to $10^{-8}$.

Ether inactivation. 8.5 ml of inoculum was added to 2.1 ml diethyl ether. The remainder of the process was similar to the chloroform inactivation experiments except that the lower phase (the aqueous phase in this experiment) was inoculated into monkeys.

Results. These experiments revealed that the virus was inactivated by ether or chloroform, using rhesus monkeys as indicators of infectivity.

As used in this invention, halogenated hydrocarbon is defined to include chloroform, Freon ® and Genetron ® fluorochloroalkane type compounds, and alkylene dichloride (such as dichloroethylene).

The ethers of this invention are selected from the $C_1$-$C_6$ alkyl groups, or lower alkyls. The ethers may be symetrical (such as the preferred diethyl ether) or asymetrical.

We claim:

1. A method of inactivating lipid viruses in blood plasma products consisting of treating said products prior to use with a treating agent selected from the group consisting of chloroform, a chloroform/lower alkanol mixure, a fluorochloro alkane and ethylene dichloride for at least about 10 minutes at a temperature of between 4°-40° C. and at 5-50% v/v.

2. A method according to claim 1 wherein the treating agent is chloroform.

3. A method according to claim 1 wherein the treating agent is a chloroform/methanol mixture.

4. A method according to claim 1 wherein the treating agent is ethylene dichloride.

* * * * *